United States Patent [19]

Irlesberger et al.

[11] Patent Number: 4,647,365
[45] Date of Patent: Mar. 3, 1987

[54] STRESS MONITORING APPARATUS FOR USE IN ELECTROFORMING AND ELECTROPLATING PROCESSES

[75] Inventors: Kurt H. Irlesberger, Longwood; Darell E. Engelhaupt, St. Cloud, both of Fla.

[73] Assignee: Martin Marietta Corporation, Bethesda, Md.

[21] Appl. No.: 756,124

[22] Filed: Jul. 18, 1985

[51] Int. Cl.$^4$ ............................................. G01N 27/42
[52] U.S. Cl. ................................... 204/434; 204/14.1
[58] Field of Search ..................... 204/1 T, 3, 7, 14.1, 204/19, 434

[56] References Cited

U.S. PATENT DOCUMENTS

| | | | |
|---|---|---|---|
| 2,568,713 | 9/1951 | Brenner | 73/150 |
| 2,829,517 | 4/1958 | Kushner | 73/150 |
| 3,215,609 | 11/1965 | Chapdelaine | 204/1 T |
| 3,356,597 | 12/1967 | Schmidt | 204/434 |
| 3,356,605 | 12/1967 | Schmidt | 204/434 |
| 3,437,568 | 4/1969 | Hasselmann et al. | 204/1 T |
| 3,570,449 | 3/1971 | Blecherman et al. | 118/9 |
| 4,086,153 | 4/1978 | Ariga et al. | 209/181 R |
| 4,086,154 | 4/1978 | Hicks | 204/195 R |

OTHER PUBLICATIONS

"The Origins of Stress in Electrodeposits I, II & III, Weil, AES Research Project 22.

Primary Examiner—Terryence Chapman
Attorney, Agent, or Firm—Gay Chin; William J. Iseman

[57] ABSTRACT

Internal stress on an object being electroplated is monitored continuously with a gauge. The gauge includes a metal receptor which is employed as a second cathode in the electrodeposition process. A separate plating current is supplied between the anode and second cathode, distinct from the separately controllable current between the anode and object being plated or electroformed. The stress on the second cathode is measured with a strain gauge, and a stress deviation from a desired plating stress is determined. The currents between the anode and first and second cathodes are adjusted in accordance with the measured internal stress on the metal receptor to achieve a desired stress condition.

The internal stress is advantageously monitored with a foil resistance strain gauge. The strain gauge is connected to a carrier disposed in parallel with the metal receptor. The carrier is rigidly connected at opposite ends to the metal receptor. A stress transmission link centrally located between ends of the metal receptor and the carrier transmits the force applied by the electroplating material on the receptor to the carrier. The strain gauge provides an indication of the stress which results from the electroplating. The currents between the anode and first and second cathodes may be controlled in accordance with this stress measurement.

6 Claims, 3 Drawing Figures

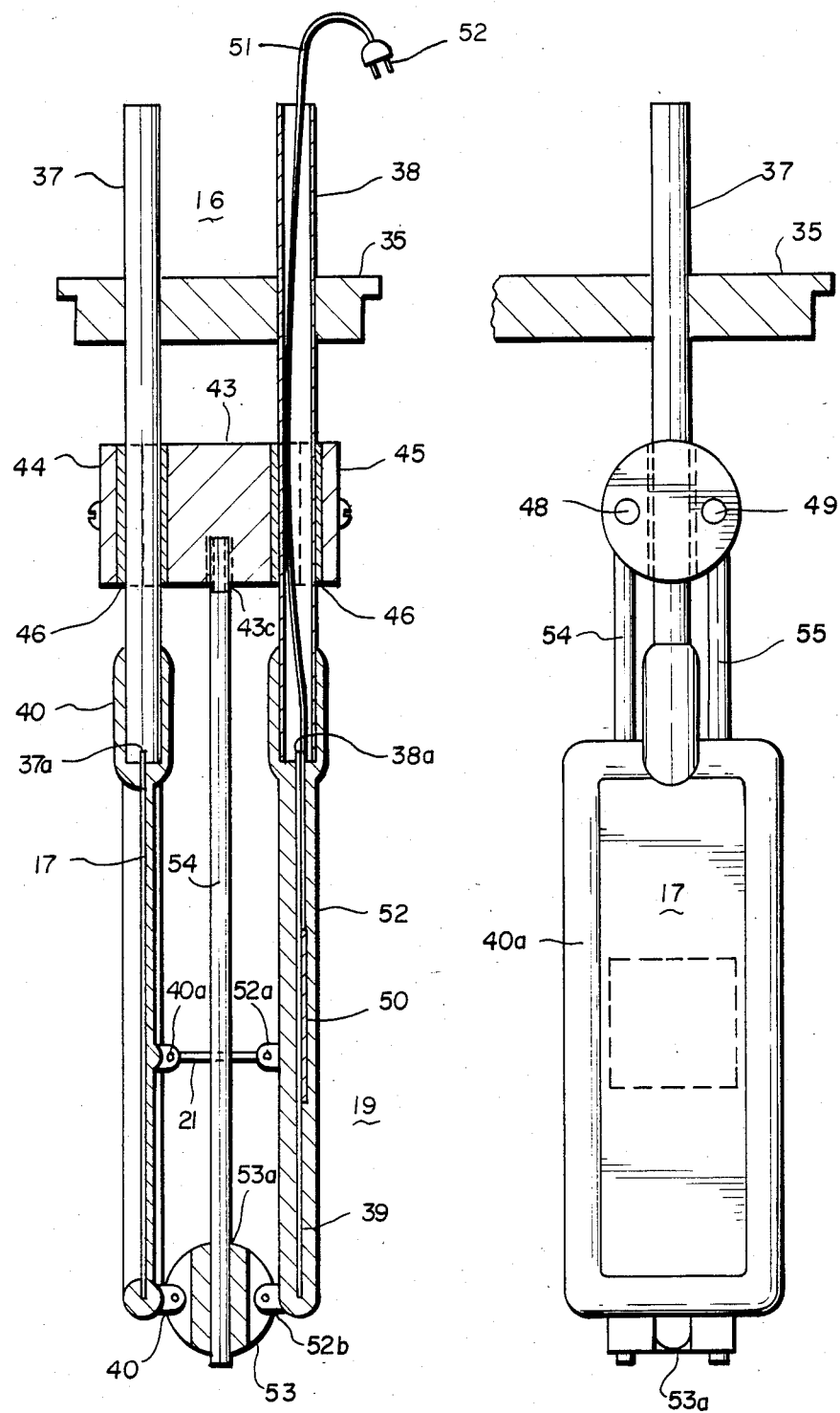

STRESS MONITORING APPARATUS FOR USE IN ELECTROFORMING AND ELECTROPLATING PROCESSES

The present invention relates to the process for accurately reproducing or plating metallic surfaces. Specifically, apparatus and methods are disclosed for accurately monitoring the stress produced during plating or electroforming on a surface of an object being plated or electroformed, and for controlling the plating deposition process in response to this stress.

Electroforming and plating processes are known in the art for metallizing surfaces of conducting bodies. In the optical arts, it is desirable to reproduce metallic surfaces having a surface accuracy of the master mandrel which remain stable over time.

Electroforming is a precision forming fabrication technique in which a part is produced by electrodepositing the desired metal on a mandrel. This electroplated metal is then built up to the desired wall thickness and separated from the mandrel.

During the metal deposition on optical surfaces the electrolytic bath chemistry changes. The metal deposition which occurs during this electrochemical change induces a change in plating induced stress on the surface of the object being plated. The change in plating stress on the object produces non-uniforming plated or electroformed parts.

Apparatus have been developed in the prior art to measure the internal stress conditions of the metal deposit formed during the electroplating process. One such device, known as the Brennex & Senderoff Spiral contractometer, allows only a spot check during the continuous electroplating.

Thus, a period of time between spot checks lapses without any indication of the stress induced during the processing.

SUMMARY OF THE INVENTION

It is an object of this invention to continuously monitor the internal stress conditions of a metal deposit received by an electroplated object.

It is a more specific object of this invention to control the current in an electroplating process to provide a constant internal stress condition for metal deposited on an electroplated object.

These and other objects are carried out by method and apparatus in accordance with the invention. Internal stress on an object being electroplated is monitored continuously with a gauge. The gauge includes a metal receptor which is employed as a second cathode in the electrodeposition process. A separate plating current is supplied between the anode and second cathode, distinct from the separately controllable current between the anode and object being plated. The stress on the second cathode is measured with a strain gauge, and a stress deviation from a desired plating stress is determined. The currents between the anode and first and second cathodes are adjusted in accordance with the measured internal stress on the metal receptor to achieve a desired stress condition.

The internal stress is advantageously monitored with a foil resistance strain gauge. The strain gauge is connected to a carrier disposed in parallel with the metal receptor. The carrier is rigidly connected at opposite ends to the metal receptor. A stress transmission link centrally located between ends of the metal receptor and the carrier transmits the force applied by the electroplating material on the receptor to the carrier. The strain gauge provides an indication of the stress which results from the electroplating. The currents between the anode and first and second cathodes may be controlled in accordance with this stress measurement.

DESCRIPTION OF THE FIGURES

FIG. 2A is a side view of a stress measuring gauge in accordance with a preferred embodiment.

FIG. 2B is another side view of the stress measuring gauge of FIG. 2A.

DESCRIPTION OF THE PREFERRED EMBODIMENT

Figure 1:
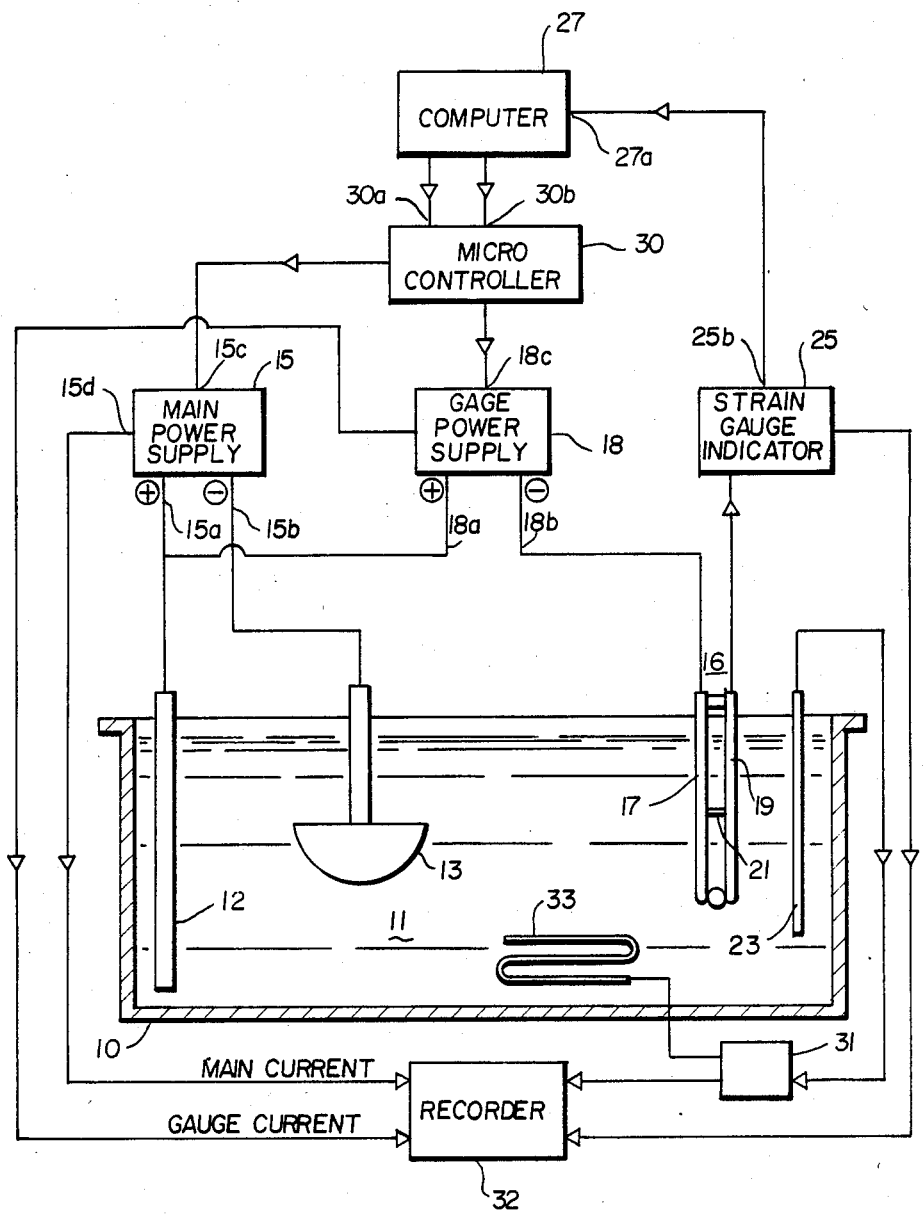
FIG. 1 is a block diagram of an apparatus for controlling an electroplating process is accordance with a preferred embodiment of the invention.

Referring now to FIG. 1, there is shown an apparatus for measuring the stress induced by plating material on an object being plated. Further, FIG. 1 demonstrates a system for controlling the electroplating current by monitoring the induced stress of metal deposits received on the object.

The system of FIG. 1 is utilized in an electroplating process having a tank 10 which holds an electroplating solution. This solution may be, as is known to those skilled in the art, a plating solution of sulfamate nickel shown as the electroplating bath 11. Disposed in the tank 10 is an anode 12. Adjacent anode 12 is an object 13 to be electroplated which comprises a cathode. Cathode 13 may be any metallic object, such as an optical surface which is to be electroplated within precise tolerances. A temperature probe 23 is disposed in the electroplating bath 11 to monitor temperature changes during electroplating over long periods of time. The temperature probe 23 will permit electroplate bath temperatures 11 to be monitored during the course of processing.

In accordance with the present invention, a gauge 16 is disposed in the electroplating bath. The gauge 16 comprises a metallic receptor 17 separated from a strain gauge carrier 19. The metallic receptor 17 is connected at both ends to the strain gauge carrier 19. A force transmission link 21 connects the metallic receptor 17 and strain gauge carrier 19 at a substantially central location.

Connected between anodes 12 and cathode 13 are the positive terminals 15a and negative terminals 15b of a main power supply 15. Main power supply 15 will supply an electroplating current which will be conducted between anode 12 and cathode 13 through the electroplating bath 11. A gauge power supply 18 is similarly connected between anode 12 and metallic receptor 17 through positive and negative terminals 18a and 18b. With the separate gauge power supply 18, it is possible to supply a separate plating current to the metallic receptor 17. The respective plating currents of cathode 13 and metallic receptor 17 which functions, as can be seen by those skilled in the art, as a second cathode, are nominally selected to a value proportional to their area. The plating currents may be advantageously selected to be approximately 0.2 amperes per square inch of surface to be plated. The metallic receptor 17 will, when receiving metallic deposits during the electroplating process, bend and impart a force through force transmission link 21 to the strain gauge carrier 19. Strain gauge carrier 19 may be conveniently read out with a strain gauge indicator 25. Thus, by monitoring the stress induced by metallic deposits on the metallic receptor 17, it is possible to determine a like stress occurring from metallic deposits on cathode 13, constituting the actual object be of interest to be electroplated.

Power supplies 15 and 18 are of a known type, for instance, in the case of main power supply 15, a Hewlett Packard 6295B, and in the case of the gauge power supply 18, Hewlett Packard HP6433B. These power supplies each have a control input 15c and 18c which permit the setting of the current supply between terminals 15a and 15b and 18a and 18b, such that the plating currents may be accurately controlled.

The strain gauge indicator 25 receives from the strain gauge carrier 19 signals produced from a foil resistance strain gauge bridge located on carrier 19. This will be more evident when referring later to FIG. 2. The differential resistance changes produced by the strain gauge bridge are converted in strain gauge indicator 25 to a digital value. One strain gauge indicator which may be utilized is a type BLH 5100, manufactured by the BLH Electronics Company, known to those skilled in the instrumentation art. The strain gauge indicator 25 of the aforesaid type will provide a digital output 25b indicating the tension or compression registered by the strain gauge bridge.

A temperature indicating controller 31 is connected to a temperature probe 23 and provides a signal indicative of the temperature of the electroplating bath 11 and also controls the immersion heater 33.

A strip recorder 32 receives as inputs the temperature indicator 31 output signal, as well as the internal stress signal from the strain gauge indicator 25. Additionally, the main current between anode 12 and cathode 13 is recorded, as well as the gauge current between anode 12 and the metallic receptor 17. Thus, recorder 32 provides an indication of the internal stress as a function of the gauge current, as well as a function of temperature and the main electroplating current. From this recording it is possible to monitor the performance of the electroplating process during a typical manufacturing run.

Control over both gauge current and main current is effected by a computer 27 which may be an HP 9826, manufactured by the Hewlett Packard Company. The computer 27 receives as an input the digital values of strain measured by the strain gauge indicator 25. The computer 27 will provide parallel outputs 30a and 30b which are weighted in accordance with the area represented by the metallic receptor 17 and cathode 13. Thus, it is possible with these weighted digital values, as computed by computer 27, to effect control over gauge power supply current and main power supply current. A microcontroller 30, which may be an HP Multiprogrammer 6942A, also manufactured by the Hewlett Packard Company, will provide a necessary interface between the control inputs 18c and 15c on the gauge power supply 18, and main power supply 15. These control inputs will, in response to the sensed stress on the metallic receptor 17, increase or decrease the currents proportionally through the gauge power supply 18, and main power supply 15. Thus, the current passing between anode 12 and cathode 13, and metallic receptor 17, also functioning as a cathode in the electroplating process, may be maintained in accordance with the sensed stress resulting from metallic deposits on the metallic receptor 17.

The main power supply 15 and gauge power supply 18 are initially set at a level which will preferably yield a zero stress reading from the strain gauge indicator 25. With this as a nominal strain, it has been found in practice that consistent plating is achieved. Of course, a nominal stress of other than zero can be selected when appropriate, by making suitable adjustments to the main power supply 15c and gauge power supply 18c nominal current supply. The control system formed by the strain gauge indicator 25 output signal, computer 27 and microcontroller 30 will thus maintain a plating current within the level to produce a metallic deposit on metallic receptor 17 within a selected nominal stress.

Referring now to FIG. 2A, there is shown a gauge 16 suitable for measuring the stress that occurs in the metal deposit.

Referring now to FIGS. 2A and 2B, there is shown in detail a gauge 16 in accordance with a preferred embodiment of the invention. The gauge 16 includes a pair of stainless steel conduits 37, 38 extending through a cover 35 of the tank 10 of FIG. 1. The extending stainless steel conduits 37 and 38 include at one end thereof a notch 37a and 38a. The notch 37a and 38a of each stainless steel conduit receives a metallic receptor 17 and a similar strain gauge metal carrier 39. The stainless steel conduits 37 and 38 are crimped in the area of notches 37a, 38a to fix the metallic receptor 17 and strain gauge metal carrier 39 in place. The metallic receptor 17 and strain gauge metal carrier 39 are sheets of stainless steel having approximately equal surface area.

The combination of a metallic receptor 17 and the crimped end of stainless steel conduit 37 are supported by an RTV or equivalent insulating carrier 40. Insulating carrier 40 is molded to cover the side of the metallic receptor 17 facing the strain gauge carrier 19. The opposite side of the metallic receptor 17 has a molded edge 40a. An exposed area of the metallic receptor 17 is provided as shown in FIG. 2B. Thus, when metallic receptor 17 becomes a cathode by applying an appropriate potential between conduit 37 and anode 12, the exposed surface area of metallic receptor 17 receives a deposit of electroplating material.

The conduits 37 and 38 are joined together by a stainless steel clamping structure 43, and associated clamps 44 and 45. The clamping structure 43 includes a stainless steel bar having a pair of grooves 43a and 43b on opposite ends, constituting a radius equivalent to the radius of stainless steel conduits 37 and 38. Clamps 44 and 45 also have a groove with a radius substantially equal to the radius of the conduits 37 and 38. Fiberglass inserts 46 and 47 are placed over the conduits 37 and 38 to provide insulation between the grooves of clamping structure 43 and the grooves of clamps 44 and 45. Clamps 44 and 45 are secured with clamping screws 48 and 49 which are received within threads located in the clamping structure 43. The conduits 37 and 38 are thus maintained horizontally fixed with respect to each other at the top thereof by the clamps 44, 45 and clamping structure 43.

The strain gauge metal carrier 39 includes a strain gauge bridge 50, such as the resistance strain gauges manufactured by the MicroMeasurement Division Company, type MA 06062AKA. These strain gauge bridges are epoxied to the rear side of the strain gauge carrier 39, and electrical connections thereto are brought up through conductor pair 51 to a plug member 52. The strain gauge metal carrier 39 is encased in an RTV housing 52 such that no portion of the strain gauge metal carrier 39, strain gauge bridge 50 or conduit 38 is exposed to the electroplating bath.

During the molding of housing 52 and insulating carrier 40, additional connection points 40a and 40b are provided, molded in the carrier RTV housing 40. Similarly, in the molding of RTV housing 52, connection points 52a and 52b are molded as well. These connection points are connected together by a sliding Teflon link 53 and a force transmission link 21.

The remaining ends of the metallic receptor 17 and strain gauge metal carrier 39 are held rigidly by a sliding Teflon link 53. Teflon link 53 includes on two sides thereof grooves 53a and 53b to accomodate two additional stiffening rods 54 and 55. Stiffening rods 54 and 55 are stainless steel and are received in openings 43c and 43d in the clamping structure 43. The Teflon sliding link 53 permits vertical movement between the ends of metallic receptor 17 and strain gauge metal carrier 39, while restricting horizontal movement during bending of receptor 17. The Teflon link 53 is joined by connecting points 52b and 40b molded into the RTV housing 52 and metallic receptor insulating carrier 40.

During electroplating, deposits of metal will form on the metallic receptor 17 exposed to the plating solution when a voltage potential between conduit 37 and anode 12 is sufficiently high. Stress which accumulates on the metallic receptor 17 as a result of the deposition and corresponding bending or receptor 17 will be transmitted via link 21 to the RTV housing 52 and thence to the strain gauge metal carrier 39. The force so applied will be measured by the strain gauge bridge 50 as a change in resistance appearing cross conductor pair 51. Plug member 52 is received in the strain gauge indicator 25 of FIG. 1. Stainless steel rods 54 and 55, in conjunction with the clamping structure 43 and sliding Teflon link 53 will result in substantially all of the force generated by the metallic deposits forming a bi-metallic interface with receptor 17 being transmitted via the transmission link 21 to the strain gauge carrier 19.

Thus, there has been described an apparatus and method for measuring the stress produced by metallic deposits formed in electroplating processes. Those skilled in the art will recognize yet other embodiments described more particularly by the claims which follow.

What is claimed is:

1. In a system having an electroplating bath, an anode submersed in said bath, an object to be plated in said bath, and a voltage potential applied between said anode and object, apparatus for monitoring the stress induced by said plating, comprising:
    first and second vertical members, supported by connection means at one end thereof a fixed distance apart, a remaining end of said vertical members being submersed in said bath;
    a plating sample receptor electrically connected to the remaining end of the first of said vertical members;
    a strain gauge carrier connected to the remaining end of said second vertical member, extending into said bath and generally parallel with said plating sample; said carrier including a strain gauge bridge connected to read changes in stress applied to said strain gauge carrier;
    spacer means connected between the free end of said strain gauge carrier and the free end of said plating sample receptor for maintaining said free ends a fixed horizontal distance apart; and
    a force transmission link connected at one end thereof to said plating sample support, and at the other end thereof to said strain gauge carrier, whereby deposition of plating material on said sample receptor imparts a measurable force through said transmission link to said strain gauge bridge, whereby changes in said stress are determined.

2. The apparatus of claim 1 further comprising a reinforcing support connected between said connection means and said spacer means.

3. The apparatus of claim 2 wherein said reinforcing support comprises a pair of spaced apart rods.

4. In a system of electroplating wherein an anode is immersed in a plating bath, an object to be plated or electroformed is immersed in said bath and a voltage potential is applied between said anode and object, apparatus for monitoring the quality of plating comprising:
    a plating sample receptor disposed in a plating bath having one surface exposed in said plating bath;
    a second voltage potential connected between said plating sample receptor and said anode;
    a strain gauge support disposed in parallel with said plating sample receptor, said support including a strain gauge bridge for measuring a force applied to said support;
    spacer means located at each end of said plating sample receptor and said strain gauge support for maintaining said ends a fixed distance apart; and
    force transmission linkage means connected between said strain gauge support and said plating sample receptor, whereby forces generated from the bimetallic interface between said plating sample receptor and received plating material are transmitted to said strain gauge bridge, said strain gauge bridge generating signals representative of said plating process.

5. The apparatus of claim 4 further comprising means for controlling an electroplating current between said anode and object in response to a current from said strain gauge bridge.

6. The apparatus of claim 4 wherein said strain gauge carrier comprises:
    a stainless steel carrier having said strain gauge bridge connected on one side thereof; and
    an insulating sheath encapsulating said steel carrier and strain gauge bridge, said insulating sheath including a coupling member for connecting to said force transmission linkage means.

* * * * *